United States Patent
Kannusamy et al.

(10) Patent No.: US 11,969,413 B2
(45) Date of Patent: Apr. 30, 2024

(54) PHARMACEUTICAL COMPOSITIONS OF DEUTETRABENAZINE AND PROCESS FOR PREPARATION THEREOF

(71) Applicant: Aurobindo Pharma Ltd, Hyderabad (IN)

(72) Inventors: Saravanan Kannusamy, Hyderabad (IN); Prabhakaran Chakkirala, Hyderabad (IN); Nagaprasad Vishnubhotla, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 0 days.

(21) Appl. No.: 17/510,797

(22) Filed: Oct. 26, 2021

(65) Prior Publication Data
US 2022/0409596 A1     Dec. 29, 2022

(51) Int. Cl.
*A61K 9/20* (2006.01)
*A61K 31/4375* (2006.01)

(52) U.S. Cl.
CPC ........ *A61K 31/4375* (2013.01); *A61K 9/2027* (2013.01); *A61K 9/205* (2013.01); *A61K 9/2054* (2013.01); *A61K 9/2077* (2013.01)

(58) Field of Classification Search
None
See application file for complete search history.

(56) References Cited

U.S. PATENT DOCUMENTS

| | | | |
|---|---|---|---|
| 10,166,183 B2 * | 1/2019 | Sommer | A61K 9/0065 |
| 2012/0202838 A1 * | 8/2012 | Ghosh | A61K 9/146 514/282 |
| 2019/0135803 A1 * | 5/2019 | Despande | C07D 455/06 |

FOREIGN PATENT DOCUMENTS

WO    WO-2018029671 A1 *   2/2018  .......... A61K 31/131

\* cited by examiner

*Primary Examiner* — Susan T Tran
(74) *Attorney, Agent, or Firm* — Jay R Akhave; Patent Science LLC

(57) ABSTRACT

This present invention relates to pharmaceutical composition comprising Deutetrabenazine. The invention also relates to the methods of preparation of the composition having improved stability and dissolution profile and used for the treatment of chorea associated with Huntington disease and tardive dyskinesia.

6 Claims, No Drawings

PHARMACEUTICAL COMPOSITIONS OF DEUTETRABENAZINE AND PROCESS FOR PREPARATION THEREOF

FIELD OF THE INVENTION

This present invention relates to pharmaceutical composition comprising Deutetrabenazine and suitable pharmaceutical excipients. The invention also relates to the methods of preparation of the composition having improved stability and dissolution profile.

BACKGROUND OF THE INVENTION

Tetrabenazine is a vesicular monoamine transporter 2 (VMAT2) inhibitor. Commonly prescribed for the treatment of Huntington's disease. Deutetrabenazine is a deuterated analogue of tetrabenazine which has improved pharmacokinetic properties when compared to non deuterated drug (tetrabenazine). Deutetrabenazine was first deuterated compound approved by FDA, used for the treatment of chorea associated with Huntington disease and tardive dyskinesia.

Deutetrabenazine is hexahydro-dimethoxybenzoquinolizine derivative and chemically known as (RR, SS)-1, 3, 4, 6, 7, 11b-hexahydro-9, 10-di(methoxy-d3)-3-(2-methylpropyl) 2H-benzo[a]quinolizin-2-one and is represented by the following formula:

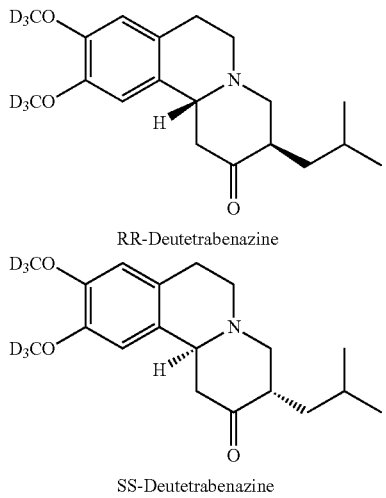

RR-Deutetrabenazine

SS-Deutetrabenazine

Deutetrabenazine is commercially available under the brand name AUSTEDO® in 6 mg, 9 mg and 12 mg film coated tablets and marketed by Teva branded pharmaceutical products in the United States. Inactive ingredients of AUSTEDO® tablets are microcrystalline cellulose, mannitol, povidone, polysorbate 80, butylated hydroxy anisole, butylated hydroxy toluene, polyethylene oxide, polyethylene glycol and magnesium stearate.

Following patent publications pertain to various formulations of Deutetrabenazine: U.S. Pat. No. 8,524,733 discloses compound deutetrabenazine or a pharmaceutically acceptable salt thereof, method of treatment of chronic hyperkinetic disorders and pharmaceutical compositions thereof.

U.S. Pat. Nos. 9,296,739; 9,233,959; 9,814,708 & 9,346,800 discloses pharmaceutical compositions of deutetrabenazine comprising mannitol, microcrystalline cellulose, polyvinyl pyrrolidone, polysorbate, poly(ethylene oxide) polymer and magnesium stearate with specific percentages.

U.S. Pat. No. 9,550,780 discloses crystalline form I and crystalline form II of deutetrabenazine.

International patent publication No. 2017/221169 discloses premixes of Deutetrabenazine with polyvinyl pyrrolidine K-30, copovidone, talc and magnesium stearate.

Published literature suggests that formulating deutetrabenazine into suitable solid oral dosage forms like tablet is challenging from the formulation development perspective due to dissolution issues, compressibility issues, manufacturing process selection, control of process and degradation of product.

Hence, there is an unmet need in the art to develop a simple, reproducible, and cost-effective manufacturing process for pharmaceutical composition of Deutetrabenazine which also offers desired pharmaceutical technical attributes such as dissolution, stability, bioequivalence and manufactured by simple, reproducible and commercially viable process at industrial scale.

The present inventors have developed solid pharmaceutical composition of Deutetrabenazine and unexpectedly found that said composition have improved stability and dissolution profile coupled with simple manufacturing process at industrial scale and it is bioequivalence to commercially available counterpart tablets) (AUSTEDO®).

SUMMARY OF THE INVENTION

In one aspect, the invention relates to a solid pharmaceutical composition comprising Deutetrabenazine with one or more pharmaceutically acceptable excipients.

In another aspect a solid pharmaceutical composition comprising:
a) 1-4% w/w of Deutetrabenazine
b) 2-10% of rate controlling polymers comprising hypromellose and xanthan gum
c) 1-10% w/w of binder comprising povidone Wherein the particle size distribution of Deutetrabenazine is such that more than 50% of the particles of Deutetrabenazine are between 150 μm to 200 μm and more than 90% of the Deutetrabenazine particles are between 350 μm to 400 μm In another aspect a solid pharmaceutical composition comprising:
a) 1-4% w/w of Deutetrabenazine
b) 2-10% of rate controlling polymers comprising hypromellose and xanthan gum
c) 1-10% w/w of binder comprising povidone Wherein the particle size distribution of Deutetrabenazine is such that more than 50% of the particles of Deutetrabenazine are between 165 μm to 175 μm and more than 90% of the Deutetrabenazine particles are between 365 μm to 375 μm In another aspect a solid pharmaceutical composition comprising:
a) 1-4% w/w of Deutetrabenazine
b) 2-10% of rate controlling polymers comprising hypromellose and xanthan gum
c) 1-10% w/w of binder comprising povidone Wherein the bulk density of lubricated blend is ranging from about 0.5 mg/mL to about 1 mg/mL and tapped density ranging from about 0.5 mg/mL to about 1 mg/mL In another aspect a solid pharmaceutical composition comprising:
a) 1-4% w/w of Deutetrabenazine with 90% of the particles having size between 360-380 μm b) 2-10% of rate controlling polymers comprising hypromellose and xanthan gum
c) 1-10% w/w of binder comprising povidone wherein not more than 50% of the Deutetrabenazine dissolves in 1 hour and at least 90% dissolves within 6 hours in a 500 ml of pH 3.0 acid phthalate buffer at a temperature of 37° C. using a USP apparatus-2 paddle over a disk at a rotation of about 75 rpm, wherein the composition is in Extended release form.

In another aspect a solid pharmaceutical composition comprising:
a) 6-12 mg of Deutetrabenazine
b) 20-30 mg of rate controlling polymers comprising hypromellose and xanthan gum
c) 10-20 mg of binder comprising povidone Wherein the particle size distribution of Deutetrabenazine is such that more than 50% of the particles of Deutetrabenazine are between 150 µm to 200 µm and more than 90% of the Deutetrabenazine particles are between 350 µm to 400 µm In another aspect a solid pharmaceutical composition comprising:
a) 6-12 mg of Deutetrabenazine
b) 20-30 mg of rate controlling polymers comprising hypromellose and xanthan gum
c) 10-20 mg of binder comprising povidone wherein not more than 50% of the Deutetrabenazine dissolves in 1 hour and at least 90% dissolves within 6 hours in a 500 ml of pH 3.0 acid phthalate buffer at a temperature of 37° C. using a USP apparatus-2 paddle over a disk at a rotation of about 75 rpm.

In another aspect a solid pharmaceutical composition comprising:
a) 6-12 mg of Deutetrabenazine
b) 20-30 mg of rate controlling polymers comprising hypromellose and xanthan gum
c) 10-20 mg of binder comprising povidone Wherein the bulk density of lubricated blend is ranging from about 0.5 mg/mL to about 1 mg/mL and tapped density ranging from about 0.5 mg/mL to about 1 mg/mL In another aspect a solid pharmaceutical composition comprising:
a) 6-12 mg of Deutetrabenazine with 90% of the particles have size between 360-380 µm
b) 20-30 mg of rate controlling polymers comprising hypromellose and xanthan gum
c) 10-20 mg of binder comprising povidone wherein not more than 50% of the Deutetrabenazine dissolves in 1 hour and at least 90% of Deutetrabenazine dissolves within 6 hours in a 500 ml of pH 3.0 acid phthalate buffer at a temperature of 37° C. using a USP apparatus-2 paddle over a disk at a rotation of about 75 rpm.

In another aspect a solid pharmaceutical composition comprising:
a) 6-12 mg of Deutetrabenazine with 90% of the particles have size between 360-380 µm,
b) 180-230 mg of mannitol;
c) 80-125 mg of microcrystalline cellulose;
d) 0.3-0.8 mg of butylated hydroxy anisole;
e) 2-6 mg of solubilizer polysorbate 80;
f) 10-16 mg of binder comprising povidone
g) 13-20 mg of hypromellose
h) 8-11 mg of xanthan gum
i) 0.1 to 0.5 mg of anti oxidant butylated hydroxy toluene
j) 1-3 mg of magnesium stearate wherein not more than 50% of the Deutetrabenazine dissolves in 1 hour and at least 90% dissolves within 6 hours in a 500 ml of pH 3.0 acid phthalate buffer at a temperature of 37° C. using a USP apparatus-2 paddle over a disk at a rotation of about 75 rpm.

In another aspect a solid pharmaceutical composition comprising:
a) Intra granular portion comprising 6-12 mg of Deutetrabenazine; 150-190 mg of mannitol; 10-16 mg povidone.
b) Extra granular portion comprising 25-40 mg mannitol; 10-20 mg hypromellose; 5-15 mg xanthan gum.

Wherein w/w ratio of hypromellose to xanthan gum is 1:0.2 to 1:0.70 and w/w ratio of Intra granular mannitol to extra granular mannitol is 1:0.15 to 1:0.40

In another aspect a solid pharmaceutical composition in the form of tablet comprising:
a) Intra granular portion comprising 2-3% of Deutetrabenazine; 45-50% of mannitol; 3-4% of povidone.
b) Extra granular portion comprising 8-10% of mannitol; 3-5% of hypromellose; 1-4% of xanthan gum.

Wherein said dosage form exhibits not more than 50% of the Deutetrabenazine dissolves in 1 hour in a 500 ml of pH 3.0 acid phthalate buffer at a temperature of 37° C. using a USP apparatus-2 paddle over a disk at a rotation of about 75 rpm.

In another aspect a solid pharmaceutical composition comprising:
a) Intra granular portion comprising 2-3% of Deutetrabenazine; 45-50% of mannitol; 3-4% of povidone.
b) Extra granular portion comprising 8-10% of mannitol; 3-5% of hypromellose; 1-4% of xanthan gum.

Wherein the loss on drying of lubricated blend at 105° C. is less than 5% w/w, 1.5-4% w/w, 1.5-3.5% w/w, 2-3.0% w/w and 2.1-2.8% and the water content for finished product are typically characterized by having a solvent loss on drying at 105° C. is less than 5% w/w, 1.5-4% w/w, 1.5-3.5% w/w, 2-3.5% w/w and 2.1-3.3%.

In another aspect, an invention provides a solid pharmaceutical composition comprising
a) 1-4% w/w of Deutetrabenazine with 90% of particles have size between 350 µm to 400 µm
b) 40-60% w/w of mannitol;
c) 19-31% w/w of microcrystalline cellulose;
d) 0.1-0.3% w/w of butylated Hydroxy anisole;
e) 1-2% w/w of polysorbate 80;
f) 3-5% w/w of povidone
g) 4-5% w/w of hypromellose
h) 2-3% w/w of xanthan gum
i) 0.01-0.2% w/w of butylated hydroxy toluene
j) 0.1-2% w/w of magnesium stearate Wherein ratio of rate controlling polymer to binder is 1:0.3 to 1:0.7 In another aspect, an invention provides a solid pharmaceutical composition comprising an intragranular phase and an extragranular phase, wherein
a) Intragranular phase comprises 1.7-3.42% w/w of Deutetrabenazine; 35-50% of mannitol; 19-31% of microcrystalline cellulose; 0.1-0.28% of butylated hydroxy anisole; 0.5-2% of polysorbate 80 and 3-4% of povidone.
b) an extra granular phase comprises 7-10% w/w of mannitol; 4-5% of hypromellose; 2-3% of xanthan gum; 0.01-0.2% of butylated hydroxy toluene and 0.3-0.8% of magnesium stearate Wherein composition has a bulk density of ranging from about 0.5 mg/mL to about 1 mg/mL.

In another aspect, an invention provides the process for producing a pharmaceutical solid dosage form which comprises steps of:
a) Mix intra granular portion excipient i.e. mannitol, microcrystalline cellulose, butylated hydroxyanisole, Deutetrabenazine, povidone and polysorbate 80 in rapid mixer granulator for 10 minutes.
b) Take isopropyl alcohol and purified water in stainless steel container to prepare solution mixture and spray the solution mixture on step a in rapid mixer granulator over a speed of not more than 3 minutes followed by kneading and discharge the wet mass.
c) Dry the wet granules of step b at an inlet temperature of 40±10° c. and further milling is done with 1.0 mm screen.
d) Mix extra granular excipients like mannitol, butylated hydroxy toluene, xanthan gum and hypromellose and add to step c and mix.
e) Add magnesium stearate to step d and mix for 5 minutes
f) Compress the lubricated blend obtained in step e on compression machine in to tablet and the tablet is further film coated.

Another aspect of an invention provides pharmaceutical composition of the present invention in the manufacture of a medicament for treating Chorea associated with Huntington's disease and tardive dyskinesia in adults.

DETAILED DESCRIPTION OF THE INVENTION

The term "composition", as in solid pharmaceutical composition, is intended to encompass a drug product comprising deutetrabenazine or its pharmaceutically acceptable salts thereof, and other inert ingredient(s). Pharmaceutical composition of the invention include, but is not limited to, granules, tablets, immediate release tablets, caplets, capsules and the like.

The term "excipient", means a pharmacologically inactive component such as a diluent, binder, disintegrant, glidant, extended release polymers, lubricant, coloring agent or the like.

The term "Deutetrabenazine" is used in broad sense to include not only "deutetrabenazine" per se but also its pharmaceutically acceptable salts, solvates, hydrates, enantiomers, derivatives, isomers, polymorphs, prodrugs thereof, and also its various crystalline and amorphous forms. According to the present invention deutetrabenazine is present in an amount from 1 to 10% by weight based on total weight of the composition, preferably, 1% to 8% w/w, more preferably 1% to 6%, most preferably 1% to 4% w/w.

The term "pharmaceutically acceptable salt" refers to salts derived from a variety of organic and inorganic counter ions including mesylate, fumarate, maleate, phosphate, L-tartrate, citrate, acetate, oxalate, and sulfate.

The term "bulk density" as used herein according to the present invention is bulk density of a powder or granules and is the ratio of the mass of an untapped powder or granules sample and its volume including the contribution of the interparticulate void volume. The bulk density is expressed in grams per milliliter (g/ml) although the international unit is kilogram per cubic meter (1 g/ml=1000 kg/m$^3$) because the measurements are made using cylinders. It may also be expressed in grams per cubic centimeter (g/cm$^3$). The bulk density of lubricated blend according to the present invention is from 0.5 g/ml to 1 g/ml, preferably from 0.6 g/ml to 0.9 g/ml, more preferably 0.6 g/ml to 0.85 g/ml and most preferably the bulk density of lubricated blend is 0.6 g/ml to 0.80 g/ml, 0.65 mg/ml to 0.75 mg/ml and more specifically 0.71 mg/ml.

The term "Tapped density" as used herein according to the present invention is an increased bulk density attained after mechanically tapping a container containing the powder sample. Tapped density is obtained by mechanically tapping a graduated measuring cylinder or vessel containing a powder sample. The tapped density is expressed in grams per milliliter (g/ml). The tapped density of lubricated blend according to the present invention is from is from 0.5 g/ml to 1 g/ml, preferably from 0.5 g/ml to 0.9 g/ml, more preferably 0.6 g/ml to 0.88 g/ml and most preferably the tapped density of lubricated blend is 0.7 g/ml to 0.87 g/ml, 0.8 mg/ml to 0.85 mg/ml and more specifically 0.81 mg/ml The term "degradation product" are unwanted chemicals that can develop during the manufacturing, transportation, and storage of drug products and can affect the efficacy of pharmaceutical products.

The dissolution is performed as per conditions mentioned or provided in office of generic drugs dissolution database and as determined by the USP. The dissolution profile of tablets dosage form was measured in 500 ml of pH 3.0 acid phthalate buffer using a USP II apparatus (Paddle) over a disk at a temperature of 37° C. and a rotation speed of 75 revolutions per minute.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent.

The term "loss on drying" is a widely used test method to determine the water content of a sample, although occasionally it may refer to the loss of any volatile matter from the sample. The step of drying is obtained by heating the granules to a temperature above room temperature and maintaining the elevated temperature, until the LOD of the granules reaches a desired value. The granules of lubricated blend are typically characterized by having a solvent loss on drying at 105° C. of less than 5% w/w, 1.5-4% w/w, 1.5-3.5% w/w, 2-3.0% w/w and 2.1-2.8% and the water content for finished product are typically characterized by having a solvent loss on drying at 105° C. of less than 5% w/w, 1.5-4% w/w, 1.5-3.5% w/w, 2-3.5% w/w and 2.1-3.3%.

The term "intra-granular/intragranular" (part/phase/portion) refers to the components of formulation of the present invention that are within granules.

The term "extra-granular/extragranular" (part/phase/portion) refers to those components of formulation of the present invention that are outside the granules.

The term "particle(s)" as used herein refers to individual particles of Deutetrabenazine or pharmaceutically acceptable salt thereof, whether the particles exist singly or are agglomerated. The term "particle size" of Deutetrabenazine having a particle size distribution such that more than 50% of the particles are between 150 μm to 200 μm most preferably 150-190 μm, 160-180 μm, 165-175 μm and more than 90% of the particles are between 350 to 400 μm, most preferably 350 to 390 μm, 360-380 μm, 365-375 μm. The particle size of Deutetrabenazine was measured using a Malvern light scattering technique.

The term "stable" as used herein refers to formulations that substantially retain the label amount of the therapeutically active ingredient during storage for commercially relevant times, and the drug-related impurity contents in the formulations remain within the acceptable limit. Wherein the assay % is within the limit from about 95-105%, preferably 98%-102%, Water by KF is within the limit from 1.5-3% and presence of total impurities are not more than 3% preferably not more than 2.4% w/w relative to Deutetrabenazine after storage for 6 months at 40° C.±2° C. and at 75% Relative humidity (RH)±5% RH.

The term "diluent" or "filler" as used herein is defined as an inert agent designed to increase the weight and/or the size of the pharmaceutical composition, for example in the case of a tablet. Examples of diluents according to present invention include, but not limited to microcrystalline cellulose, silicified MCC, microfine cellulose, anhydrous lactose, lactose monohydrate, mannitol and mixtures thereof. Diluent is present in an amount from 50 to 90%. Preferably, the amount of diluent is from 55% to 90% w/w, more preferably, the amount of diluent is from 65% to 95% w/w, and preferred diluents according to the present invention is microcrystalline cellulose and mannitol, wherein ratio of Intra granular mannitol to Extra granular mannitol 1:0.15, 1:0.16, 1:0.17, 1:0.18, 1:0.19, 1:0.20, 1:0.25, 1:0.30, 1:0.35, 1:0.40.

The term "binder" as used herein is defined as an agent able to bind particles which cannot be bound only by a compression force. Examples of binders include, but are not limited to acacia, dextrin, ethyl cellulose, hydroxypropyl cellulose, hydroxypropyl methylcellulose, carboxymethyl cellulose sodium, povidone and/or mixtures thereof. Binder is present in an amount from 1-10% w/w. preferably, the amount of binder is from 1-8% w/w, more preferably the amount of binder is from 2-7% w/w most preferably the amount of binder is 3-5% w/w and preferred binder according to the present invention is Povidone. wherein Ratio of rate controlling polymer to binder is 1:0.40, 1:0.50, 1:0.55, 1:0.56, 1:0.57, 1:0.58, 1:0.60.

The term "lubricant" as used herein is defined as an agent able to decrease adhesion of a powder to punches and friction between particles. The lubricant may be present in the pharmaceutical composition in the form of a single compound or in the form of a mixture of compounds. Examples of lubricants according to present invention include, but not limited to stearic acid, Zinc stearate, sodium stearyl Fumarate, magnesium stearate. Lubricant is present in an amount from 0.5 to 3%, preferably, the amount of lubricant is from 0.1% to 2% w/w, preferred lubricant according to the present invention is magnesium stearate.

The term "antioxidant" is intended to mean an agent that inhibits oxidation and thus is used to prevent the deterioration of preparations by the oxidative process. Wherein anti-oxidant is selected from the group consisting of butylated hydroxyanisole, butylated hydroxytoluene and sodium ascorbate. Antioxidants are present in an amount from 0.1% to 0.5%, preferred Antioxidants according to the present invention is hydroxyanisole and butylated hydroxytoluene.

The term "Solubilizer" is intended to provide better wettability and enhance the solubility of the drug, which improves the dissolution property. Wherein Solubilizer is selected from the group consisting of sodium lauryl sulphate, sodium cetyl stearyl sulphate or sodium dioctyl sulphosuccinate, lecithin, cetyl alcohol, stearyl alcohol, cetyl stearyl alcohol, cholesterol, sorbitan fatty acid esters such as sorbitan mono-oleate, polyoxyethylene sorbitan fatty acid esters such as polysorbate 80, polysorbate 20, polyoxyethylene fatty acid glycerides such as macrogol 1000 glycerol monostearate, polyoxyethylene fatty acid esters such as polyoxyl 40 stearate, polyoxyethylene fatty alcohol ethers such as polyoxyl 10 oleyl ether, glycerol fatty acid esters such as glycerol monostearate. Solubilizer is present in an amount from 0.5% to 2%, preferred Solubilizer according to the present invention is polysorbate 80.

The term "rate controlling polymer" include all excipients and/or polymers that control the release of a pharmaceutical agent(s) after administration in a subject. Examples of release excipients or rate controlling polymers include, but are not limited to, hypromellose, hydroxypropyl cellulose, xanthan gum, ethyl cellulose and prop-2-enoic acid. Ratio of release controlling polymers hypromellose to xanthan gum is 1:0.20, 1:0.30, 1:0.40, 1:0.50, 1:0.60, 1:0.61, 1:0.65, 1:0.70.

The term "extended release" used herein refer to a dosage form that provides gradual release of Deutetrabenazine over an extended period of time.

The term "coated tablet" as used herein is defined as an tablet provided with a coating layer is preferable to achieve long-term storage stability and prevent degradation due to light and the like. The coating layer comprise pharmaceutical additives, such as a coating agent, plasticizer, dispersant, defoaming agent, and the like, usually used for coating (for providing a coat to) orally administrable pharmaceutical preparations. Colorants are added to the coating agent for coating the tablet. Examples of film coating material includes Opadry which is Colorcon's customized, one-step film coating system which combines polymer, plasticizer, opacifier and pigment, as required, in a dry concentrate. Examples of Opadry coating material according to present invention include, but not limited to Opadry yellow, Opadry orange, Opadry white.

Composition of Opadry orange contains polyvinyl alcohol, titanium dioxide, polyethylene glycol, talc and iron oxide yellow and iron oxide red.

In one embodiment, the invention relates to a solid pharmaceutical composition comprising Deutetrabenazine with one or more pharmaceutically acceptable excipients.

In one embodiment, an invention provides a solid pharmaceutical composition comprising:
  a) 1-4% w/w of Deutetrabenazine
  b) 2-10% of rate controlling polymers comprising hypromellose and xanthan gum
  c) 1-10% w/w of binder comprising povidone
  Wherein the particle size distribution of Deutetrabenazine is such that more than 50% of the particles of Deutetrabenazine are between 150 µm to 200 µm and more than 90% of the Deutetrabenazine particles are between 350 µm to 400 µm In another embodiment, an invention provides a solid pharmaceutical composition comprising:
  a) 1-4% w/w of Deutetrabenazine with 90% of the particles having size between 360-380 µm
  b) 2-10% of rate controlling polymers comprising hypromellose and xanthan gum
  c) 1-10% w/w of binder comprising povidone
  wherein not more than 50% of the Deutetrabenazine dissolves in 1 hour and at least 90% dissolves within 6 hours in a 500 ml of pH 3.0 acid phthalate buffer at a temperature of 37° C. using a USP apparatus-2 paddle over a disk at a rotation of about 75 rpm.

In one embodiment, an invention provides a solid pharmaceutical composition comprising:
  a) 6-12 mg of Deutetrabenazine
  b) 20-30 mg of rate controlling polymers comprising hypromellose and xanthan gum
  c) 10-20 mg of binder comprising povidone
  Wherein the particle size distribution of Deutetrabenazine is such that more than 50% of the particles of Deutetrabenazine are between 150 μm to 200 μm and more than 90% of the Deutetrabenazine particles are between 350 μm to 400 μm In another embodiment, an invention provides a solid pharmaceutical composition comprising:
a) 6-12 mg of Deutetrabenazine
b) 20-30 mg of rate controlling polymers comprising hypromellose and xanthan gum
c) 10-20 mg of binder comprising povidone
wherein not more than 50% of the Deutetrabenazine dissolves in 1 hour and at least 90% dissolves within 6 hours in a 500 ml of pH 3.0 acid phthalate buffer at a temperature of 37° C. using a USP apparatus-2 paddle over a disk at a rotation of about 75 rpm.

In one embodiment, an invention provides a solid pharmaceutical composition comprising:
a) 6-12 mg of Deutetrabenazine with 90% of the particles have size between 360-380 μm,
b) 180-230 mg of mannitol;
c) 80-125 mg of microcrystalline cellulose;
d) 0.3-0.8 mg of butylated hydroxy anisole;
e) 2-6 mg of solubilizer polysorbate 80;
f) 10-16 mg of binder comprising povidone
g) 13-20 mg of hypromellose
h) 8-11 mg of xanthan gum
i) 0.1 to 0.5 mg of anti oxidant butylated hydroxy toluene
j) 1-3 mg of magnesium stearate
wherein not more than 50% of the Deutetrabenazine dissolves in 1 hour and at least 90% dissolves within 6 hours in a 500 ml of pH 3.0 acid phthalate buffer at a temperature of 37° C. using a USP apparatus-2 paddle over a disk at a rotation of about 75 rpm.

In another embodiment, an invention provides a solid pharmaceutical composition comprising:
a) Intra granular portion comprising 6-12 mg of Deutetrabenazine; 150-190 mg of mannitol; 10-16 mg povidone.
b) Extra granular portion comprising 25-40 mg mannitol; 10-20 mg hypromellose; 5-15 mg xanthan gum.
Where w/w ratio of hypromellose to xanthan gum is 1:0.2 to 1:0.70 and w/w ratio of Intra granular mannitol to extra granular mannitol is 1:0.15 to 1:0.40

In one embodiment, an invention provides a solid pharmaceutical composition comprising:
a) Intra granular portion comprising 2-3% of Deutetrabenazine; 45-50% of mannitol; 3-4% of povidone.
b) Extra granular portion comprising 8-10% of mannitol; 3-5% of hypromellose; 1-4% of xanthan gum.
Wherein said dosage form exhibits not more than 50% of the Deutetrabenazine dissolves in 1 hour in a 500 ml of pH 3.0 acid phthalate buffer at a temperature of 37° C. using a USP apparatus-2 paddle over a disk at a rotation of about 75 rpm.

In another embodiment, an invention provides a solid pharmaceutical composition comprising:
a) Intra granular portion comprising 2-3% of Deutetrabenazine; 45-50% of mannitol; 3-4% of povidone.
b) Extra granular portion comprising 8-10% of mannitol; 3-5% of hypromellose; 1-4% of xanthan gum.
Wherein the loss on drying of lubricated blend at 105° C. is less than 5% w/w, 1.5-4% w/w, 1.5-3.5% w/w, 2-3.0% w/w and 2.1-2.8% and the water content for finished product are typically characterized by having a solvent loss on drying at 105° C. is less than 5% w/w, 1.5-4% w/w, 1.5-3.5% w/w, 2-3.5% w/w and 2.1-3.3%.

In one embodiment, an invention provides a solid pharmaceutical composition comprising intragranular phase and an extragranular phase, wherein
a) Intragranular phase comprises 1.7-3.42% w/w of Deutetrabenazine; 35-50% of mannitol; 19-31% of microcrystalline cellulose; 0.1-0.28% of butylated hydroxy anisole; 0.5-2% of polysorbate 80 and 3-4% of povidone.
b) an extra granular phase comprises 7-10% w/w of mannitol; 4-5% of hypromellose; 2-3% of xanthan gum; 0.01-0.2% of butylated hydroxy toluene and 0.3-0.8% of magnesium stearate
wherein composition has a bulk density of ranging from about 0.5 mg/mL to about 1 mg/mL.

In one embodiment, an invention provides a process for producing a pharmaceutical solid dosage form which comprises steps of:
a) Mix intra granular portion excipient i.e. mannitol, microcrystalline cellulose, butylated hydroxyanisole, Deutetrabenazine, povidone and polysorbate 80 in rapid mixer granulator for 10 minutes.
b) Take isopropyl alcohol and purified water in stainless steel container to prepare solution mixture and spray the solution mixture on step a in rapid mixer granulator over a speed of not more than 3 minutes followed by kneading and discharge the wet mass.
c) Dry the wet granules of step b at an inlet temperature of 40±10° c. and further milling is done with 1.0 mm screen.
d) Mix extra granular excipients like mannitol, butylated hydroxy toluene, xanthan gum and hypromellose and add to step c and mix.
e) Add magnesium stearate to step d and mix for 5 minutes
f) Compress the lubricated blend obtained in step e on compression machine in to tablet and the tablet is further film coated.

Surprisingly, it has been found that the pharmaceutical composition of the present invention has been found to have improved stability and dissolution profile coupled with simple manufacturing process at industrial scale and it is bioequivalence to commercially available counterpart tablets AUSTEDO®.

The following examples serve to illustrate the embodiments of the present invention. However, they do not intend to limit the scope of the invention. It is obvious to those skilled in the art to find out the composition for other dosage forms and substitute the equivalent excipients as described in this specification or with the one known to the industry.

EXAMPLES

The following examples further illustrate the invention and do not limit the scope of the invention.

Example 1: Deutetrabenazine Tablets were Prepared by Using Quantitative Formulas as Given in Table 1

TABLE 1

| S. No | Ingredients | Example 1 in mg | | | % |
|---|---|---|---|---|---|
| | Intra granular | | | | |
| 1 | Deutetrabenazine | 6.0 | 9.0 | 12.0 | 1.7-3.4 |
| 2 | Mannitol Part-I | 134.8 | 134.8 | 134.8 | 47.1 |
| 3 | Mannitol Part-II | 33.7 | 33.7 | 33.7 | |
| 4 | Microcrystalline cellulose Part I | 78.4 | 76.0 | 73.6 | 25.7-27.4 |
| 5 | Microcrystalline cellulose Part II | 19.6 | 19.0 | 18.4 | |

TABLE 1-continued

| S. No | Ingredients | Example 1 in mg | | | % |
|---|---|---|---|---|---|
| 6 | Butylated Hydroxy anisole | 0.5 | 0.5 | 0.5 | 0.2 |
| 7 | Polysorbate 80 | 4 | 4 | 4 | 1.1 |
| 8 | Povidone | 14 | 14 | 14 | 3.9 |
| | Granulating fluid | | | | |
| 9 | Isopropyl alcohol | q.s | q.s | q.s | — |
| 10 | Purified water | q.s | q.s | q.s | — |
| | Extra granular | | | | |
| 11 | Mannitol | 31.9 | 31.9 | 31.9 | 8.9 |
| 12 | Hypromellose | 15.5 | 15.5 | 15.5 | 4.4 |
| 13 | Xanthan gum | 9.5 | 9.5 | 9.5 | 2.7 |
| 14 | Butylated hydroxy toluene | 0.3 | 0.3 | 0.3 | 0.08 |
| 15 | Magnesium stearate | 1.7 | 1.7 | 1.7 | 0.5 |
| | Film coating | | | | |
| 16 | Opadry II Yellow/Orange/White | 9.1 | 9.1 | 9.1 | 2.5 |
| 19 | Purified water | q.s | q.s | q.s | — |
| | Weight of coated tablet | 357.0 | 357.0 | 357.0 | |

Manufacturing Process:
 a) Mix mannitol, microcrystalline cellulose, butylated hydroxyanisole, Deutetrabenazine, povidone and polysorbate 80 of Intra granular part in rapid mixer granulator for 10 minutes.
 b) Take isopropyl alcohol and purified water in stainless steel container to prepare solution mixture and spray the solution mixture on step a in rapid mixer granulator over a speed of not more than 3 minutes followed by kneading and discharge the wet mass.
 c) Dry the wet granules of step b at an inlet temperature of 40±10° c. and further milling is done with 1.0 mm screen.
 d) Mix extra granular excipients like mannitol, butylated hydroxy toluene, xanthan gum and hypromellose and add to step c and mix.
 e) Add magnesium stearate to step d and mix for 5 minutes
 f) Compress the lubricated blend obtained in step e on compression machine in to tablet and the tablet is furtherly film coated.

Example 2: Deutetrabenazine Tablets were Prepared by Using Quantitative Formulas as Given in Table 2

TABLE 2

| S. No | Ingredients | Example 2 in mg | | | % |
|---|---|---|---|---|---|
| | Intra granular | | | | |
| 1 | Deutetrabenazine | 6.0 | 9.0 | 12.0 | 2.1-2.9 |
| 2 | Mannitol Part-I | 154.8 | 154.8 | 154.8 | 47.7-45.7 |
| 3 | Mannitol Part-II | 33.7 | 33.7 | 33.7 | |
| 4 | Microcrystalline cellulose Part I | 88.2 | 104.5 | 101.2 | 27.3-29.8 |
| 5 | Microcrystalline cellulose Part II | 19.6 | 19.0 | 18.4 | |
| 6 | Butylated Hydroxy anisole | 0.5 | 0.5 | 0.5 | 0.1 |
| 7 | Polysorbate 80 | 4.4 | 4.4 | 4.4 | 1.0-1.1 |
| 8 | Povidone | 15.4 | 15.4 | 15.4 | 3.7-3.9 |
| | Granulating fluid | | | | |
| 9 | Isopropyl alcohol | q.s | q.s | q.s | — |
| 10 | Purified water | q.s | q.s | q.s | — |
| | Extra granular | | | | |
| 11 | Mannitol | 31.9 | 31.9 | 31.9 | 7.7-8.0 |
| 12 | Hypromellose | 17 | 17 | 17 | 4.1-4.3 |
| 13 | Xanthan gum | 10.4 | 10.4 | 10.4 | 2.5-2.6 |
| 14 | Butylated hydroxy toluene | 0.3 | 0.3 | 0.3 | 0.07-0.08 |
| 15 | Magnesium stearate | 1.9 | 1.9 | 1.9 | 0.46-0.48 |
| | Film coating | | | | |
| 16 | Opadry II Yellow/Orange/White | 10.1 | 10.1 | 10.1 | 2.44-2.56 |
| 19 | Purified water | q.s | q.s | q.s | — |
| | Weight of coated tablet | 394.4 | 413.1 | 412.2 | |

Manufacturing Process:
 Same as example 1

Example 3: Deutetrabenazine Tablets

TABLE 3

| S. no | Ingredients | Quantity 3 in mg | % |
|---|---|---|---|
| 1 | Deutetrabenazine | 6-12 | |
| 2 | Mannitol Part-I | 130-140 | 30-40% |
| 3 | Mannitol Part-II | 30-40 | 5-10% |
| 4 | Microcrystalline cellulose Part I | 70-80 | 15-25% |
| 5 | Microcrystalline cellulose Part II | 15-25 | 4-6% |
| 6 | Butylated Hydroxy anisole | 0.4-0.7 | 0.1-0.2% |
| 7 | Polysorbate 80 | 2-6 | 0.5-2% |
| 8 | Povidone | 10-15 | 3-4% |
| | Granulating fluid | | |
| 9 | Isopropyl alcohol | q.s | — |
| 10 | Purified water | q.s | — |
| | Extra granular | | |
| 11 | Mannitol | 30-40 | 9-10% |
| 12 | Hypromellose | 14-20 | 4-5% |
| 13 | Xanthan gum | 8-10 | 2-3% |
| 14 | Butylated hydroxy toluene | 0.1-0.5 | 0.01-0.2% |
| 15 | Magnesium stearate | 1-3 | 0.3-0.8% |
| | Film coating | | |
| 16 | Opadry II Yellow/Orange/White | 5-10 | 1.4-2.4% |
| 19 | Purified water | q.s | — |
| | Weight of coated tablet | 321.5-403.2 | 100% |

Manufacturing Process: Same as Example 1

TABLE 2

Properties of lubricated blend and final product as per examples 1-3:

| S. no | Elements | Results |
|---|---|---|
| 1 | Bulk Density (lubricated blend) | 0.71 ± 0.06 g/ml |
| 2 | Tapped Density (lubricated blend) | 0.81 ± 0.05 g/ml |
| 3 | Water content (lubricated blend) | 2.2-2.5% w/w |
| 4 | Water content (lubricated blend) | 2.4-2.9% w/w |

Dissolution study: The dissolution profile of the tablets (6 mg, 9 mg and 12 mg) prepared using quantitative composition as mentioned in example 1-3 is shown in Table 3 below.

Dissolution Conditions:
 pH 3.0 acid phthalate buffer, 500 mL, USP Apparatus II (Paddle) over a disk, 75 RPM, 37° C.±5° c.

Table 3: Dissolution profile of commercially marketed Deutetrabenazine tablets (AUSTEDO®) and Example 1,

TABLE 3

| | Strength | | | | | |
|---|---|---|---|---|---|---|
| | 6 mg | | 9 mg | | 12 mg | |
| | | | Product | | | |
| Time points | AUSTEDO | Example 1 | AUSTEDO | Example 1 | AUSTEDO | Example 1 |
| | | | % Deutetrabenazine released (±5%) | | | |
| 0.5 hr | 23 | 26 | 19 | 23 | 20 | 26 |
| 1 hr | 36 | 35 | 30 | 40 | 31 | 33 |
| 1.5 hr | 49 | 46 | 40 | 50 | 42 | 49 |
| 2 hr | 59 | 59 | 50 | 62 | 50 | 59 |
| 3 hr | 79 | 85 | 66 | 88 | 67 | 81 |
| 4 hr | 93 | 93 | 86 | 95 | 90 | 92 |
| 5 hr | 92 | 96 | 91 | 97 | 91 | 93 |
| 6 hr | 93 | 96 | 93 | 98 | 91 | 94 |

The dissolution profiles of AUSTEDO® and Example 1 are considered similar based on f1 and f2 results of above table.

Stability Studies:

Tablet dosage form prepared in Example 1 was subjected to Accelerated stability testing as per the ICH guidelines at temperature 40°±2° C. and relative humidity of 75%±5% for 6 months and evaluated the data at 3 months and 6 months. The tablet dosage form was placed in a high density polyethylene (HDPE) bottles exposed to above mentioned condition and then evaluated for Assay %, Water by KF, Related substances and Dissolution which is shown in Table 4:

TABLE 4

Results of Assay, Water by KF, Related substances and Dissolution data on stability samples for Example 1:

| | | Condition | | | | | | | | |
|---|---|---|---|---|---|---|---|---|---|---|
| | | RT | 40° C. ± 2° C./75 % RH ± 5% RH | | RT | 40° C. ± 2° C./75% RH ± 5% RH | | RT | 40° C. ± 2° C./75% RH ± 5% RH | |
| | | | | | | Period | | | | |
| | | Initial | 3 M | 6 M | Initial | 3 M | 6 M | Initial | 3 M | 6 M |
| | | | 6 mg | | | 9 mg | | | 12 mg | |
| 1 | Assay (%) | 101.5 | 98.5 | 99.2 | 100.5 | 98.9 | 100.2 | 101.2 | 100.8 | 101.8 |
| 2 | Water by KF % | 2.41 | 2.85 | 2.61 | 2.23 | 2.12 | 2.05 | 2.27 | 2.11 | 1.93 |
| | Related substances % | | | | | | | | | |
| 3 | Deutetrabenazine N-oxide Isomers | 0.02 | 0.11 | 0.11 | 0.02 | 0.09 | 0.11 | 0.02 | 0.04 | 0.05 |
| | Dehydro Deutetrabenazine | 0.07 | 0.30 | 0.35 | 0.07 | 0.23 | 0.28 | 0.14 | 0.18 | 0.20 |
| | (SR/RS)-Diastereomers | 0.37 | 1.51 | 1.75 | 0.25 | 0.99 | 1.26 | 0.18 | 0.76 | 0.70 |
| | Any other Invidual impurity | 0.04 | 0.06 | 0.09 | 0.04 | 0.05 | 0.07 | ND | ND | ND |
| | Total | 0.51 | 1.99 | 2.31 | 0.40 | 1.36 | 1.75 | 0.34 | 0.98 | 0.95 |
| | Dissolution | % Deutetrabenazine released (±5%) | | | | | | | | |
| 4 | 0.5 hr | 26 | 24 | 23 | 23 | 24 | 25 | 26 | 20 | 23 |
| | 1 hr | 35 | 36 | 36 | 40 | 38 | 41 | 33 | 37 | 41 |
| | 1.5 hr | 46 | 45 | 47 | 50 | 46 | 47 | 49 | 53 | 55 |
| | 2 hr | 59 | 56 | 61 | 62 | 59 | 61 | 59 | 60 | 63 |
| | 3 hr | 85 | 85 | 87 | 88 | 85 | 85 | 81 | 84 | 85 |
| | 4 hr | 93 | 90 | 93 | 95 | 92 | 93 | 92 | 93 | 93 |
| | 5 hr | 96 | 93 | 95 | 97 | 95 | 96 | 93 | 96 | 95 |
| | 6 hr | 96 | 96 | 98 | 98 | 96 | 98 | 94 | 97 | 97 |

The present formulation clearly indicates excellent chemical stability upon storage at accelerated stability conditions at 40°±2° C. and 75%±5% relative humidity for six months.

We claim:

1. An extended release tablet composition comprising,
   a) 1-4% w/w of Deutetrabenazine with 90% of the particles having size between 360-380 μm b) 2-10% w/w of rate controlling polymers consisting of a combination of hypromellose and xanthan gum in a w/w ratio of 1:0.2 to 1:0.70 c) 1-10% w/w of povidone as binder, wherein ratio of rate controlling polymer to binder is 1:0.3 to 1:0.7 and the composition contains not more than 2.4% of total impurities by weight relative to Deutetrabenazine after storage for 6 months at 40° C.±2° C./75% RH±5% RH and not more than 50% of the Deutetrabenazine dissolves in 1 hour and at least 90% dissolves within 6 hours in a 500 ml of pH 3.0 acid phthalate buffer at a temperature of 37° C. using a USP apparatus-2 paddle over a disk at a rotation of about 75 rpm, wherein the composition is free of surfactant.

2. An extended release tablet composition comprising, a) 6-12 mg of Deutetrabenazine with 90% of the particles having size between 360-380 μm b) 20-30 mg of rate controlling polymers consisting of a combination of hypromellose and xanthan gum in a w/w ration of 1:0.2 to 1:0.70 c) 10-20 mg of povidone as binder wherein ratio of rate controlling polymer to binder is 1:0.3 to 1:0.7 and the composition contains not more that 2.4% of total impurities by weight relative to Deutetravenazine after storate for 6 months at 40 ° C.±2° C./75% RH±5% RH and not more than 50% of the Deutetrabenazine dissolves in 1 hour and at least 90% of Deutetrabenazine dissolves within 6 hours in a 500 ml of pH 3.0 acid phthalate buffer at a temperature of 37° C. using a USP apparatus-2 paddle over a disk at a rotation of about 75 rpm, wherein the composition is free of surfactant.

3. An extended release table composition comprising, a) intra granular portion comprising 2-3% of Deutetrabenazine; 45-50% of mannitol; 3-4% of povidone b) extra granular portion comprising 8-10% of mannitol; 3-5% of hypromellose; 1-4% of xanthan gum wherein the composition contains not more than 2.4% of total impurities by weight relative to Deutetrabenazine after storage for 6 months at 40° C.±2° C./75% RH±5% RH and said dosage form exhibits not more than 50% of the Deutetrabenazine dissolved in 1 hour in a 500 ml of pH 3.0 acid phthalate buffer at a temperature of 37° C. using a USP apparatus-2 paddle over a disk at a rotation of about 75 rpm, wherein the composition is free of surfactant.

4. The extended release tablet composition according to claim 3 wherein w/w ratio of intra granular mannitol to extra granular mannitol is 1:0.15 to 1:0.40.

5. The extended release tablet composition according to claim 3 wherein particle size distribution of Deutetrabenazine is such that more than 50% of the particles of Deutetrabenazine are between 165 μm to 175 μm and more than 90% of the Deutetrabenazine particles are between 365μm to 375μm.

6. The extended release composition according to claim 3 wherein loss on drying of finished tablet at 105° C. in the range of 1.5-3.5% w/w.

* * * * *